United States Patent
Mallouk et al.

(10) Patent No.: US 6,284,402 B1
(45) Date of Patent: Sep. 4, 2001

(54) ELECTROCATALYST COMPOSITIONS

(75) Inventors: Thomas E. Mallouk; Benny C. Chan, both of State College, PA (US); Erik Reddington, Woburn, MA (US); Anthony Sapienza, West Chester; Guoying Chen, State College, both of PA (US); Eugene Smotkin, Chicago, IL (US); Bogdan Gurau, Chicago, IL (US); Rameshkrishnan Viswanathan, Chicago, IL (US); Renxuan Liu, Chicago, IL (US)

(73) Assignees: The Penn State Research Foundation, University Park, PA (US); The Illinois Institute of Technology, Chicago, IL (US)

( * ) Notice: Subject to any disclaimer, the term of this patent is extended or adjusted under 35 U.S.C. 154(b) by 0 days.

(21) Appl. No.: 09/326,206

(22) Filed: Jun. 4, 1999

Related U.S. Application Data
(60) Provisional application No. 60/088,294, filed on Jun. 5, 1998.

(51) Int. Cl.[7] .............................. H01M 4/86; H01M 4/90; H01M 4/96; H01M 4/58
(52) U.S. Cl. ........................... 429/40; 429/45; 429/218.1
(58) Field of Search .............................. 429/218, 40, 45; 502/325, 339

(56) References Cited

U.S. PATENT DOCUMENTS

| | | |
|---|---|---|
| 3,428,490 | 2/1969 | Bravo et al. . |
| 3,506,494 * | 4/1970 | Adlhart ................................. 136/86 |
| 4,127,468 | 11/1978 | Alfenaar et al. . |
| 4,186,110 * | 1/1980 | Jalan et al. ........................... 252/447 |
| 4,192,907 | 3/1980 | Jalan et al. . |
| 4,447,506 * | 5/1984 | Luczak et al. ........................ 429/44 |
| 4,548,921 * | 10/1985 | Geus et al. ........................... 502/330 |
| 4,657,888 | 4/1987 | Mesters et al. . |
| 4,880,711 | 11/1989 | Luczak et al. . |
| 4,925,747 | 5/1990 | Kordesch et al. . |
| 5,133,843 * | 7/1992 | Eisman ............................. 204/105 R |
| 5,162,169 | 11/1992 | Tomantschger et al. . |
| 5,208,207 | 5/1993 | Stonehart et al. . |
| 5,225,391 | 7/1993 | Stonehart et al. . |
| 5,286,580 | 2/1994 | Ippommatsu et al. . |
| 5,316,643 * | 5/1994 | Ahn et al. .............................. 204/265 |
| 5,599,640 | 2/1997 | Lee et al. . |
| 5,605,662 | 2/1997 | Heller et al. . |
| 5,759,944 | 6/1998 | Buchanan et al. . |
| 5,856,036 | 1/1999 | Smotkin et al. . |
| 5,876,867 | 3/1999 | Itoh et al. . |
| 5,959,297 | 9/1999 | Weinberg et al. . |

OTHER PUBLICATIONS

Gasteiger, H., et al., CO Electrooxidation on Well–Characterized Pt–Ru Allowy, J. Phys. Chem., 98:617–625 (1994).
Ley, K., et al., Methanol Oxidation on Single–Phase Pt–Ru–Os Ternary Alloys, J. Electrochem. Soc., 144:1543 (1997).
Reddington et al., Combinatorial Electrochemistry: A Highly Parallel, Optical Screening Method for Discovery of Better Electrocatalysts, Science 280:267 (1998).
Zuckermann, R., et al., Discovery of Nanomolar Ligands for 7–Transmembrane G–Protein–Coupled Receptors from a Diverse N–(Substituted) glycine Petptoid Library, J. Med. Chem., 37:2678–2685 (1994).
McKee, D.W., et al., Catalytic Activity of Noble Metal Alloys. Methane–Deuterium Exchange and Propane Cracking on Platinum–Palladium and Palladium–Rhodium Alloys, J. of Catalysis, 3:252–267 (1964).
McKee, D.W., Catalytic Decomposition of Hydrogen Peroxide by Metals and Alloys of the Platinum Group, J. of Catalysis, 14:355–364 (1969).
Marczencko, Z, Separation and Spectrophotometric Determination of Elements, ch. 32, Ellis Horwood publ., Chichester (1986).
Watanabe et al., Preparation of Highly Dispersed Pt+Ru Alloy Clusters and the Activity for the Electrooxidation of Methanol, J. Electroanal. Chem., 229:395–406 (1987).

* cited by examiner

Primary Examiner—Tom Dunn
Assistant Examiner—Zidia Pittman
(74) Attorney, Agent, or Firm—Ohlandt, Greeley, Ruggiero & Perle, L.L.P.

(57) ABSTRACT

Compositions for use as catalysts in electrochemical reactions are described. The compositions are alloys prepared from two or more elemental metals selected from platinum, molybdenum, osmium, ruthenium, rhodium, and iridium. Also described are electrode compositions including such alloys and electrochemical reaction devices including such catalysts.

14 Claims, 4 Drawing Sheets

ELECTROCATALYST COMPOSITIONS

CROSS-REFERENCE TO RELATED APPLICATIONS

This present application claims the benefit of provisional application Ser. No. 60/088,294 filed Jun. 5, 1998, which is incorporated herein by reference.

STATEMENT AS TO FEDERALLY-SPONSORED RESEARCH

This invention was made with Government support under grants DAAH04-94-G-0055, DAAH04-95-0330, awarded by the U.S. Army Research Office and DARPA as well as from Contract No. DE-FGO2-93ER14374 awarded by the Department of Energy and Subcontract No. SA151-298 by the U.S. Army Research Office and DARPA. The Government may have certain rights in the invention.

FIELD OF THE INVENTION

The invention relates to compositions useful as electrocatalysts in electrochemical reactor devices. More particularly, this invention relates to metal alloys that can be used as anodes or cathodes in fuel cells.

BACKGROUND OF THE INVENTION

Many chemical reactions are thermodynamically favorable, but do not occur at useful rates in the absence of substances which catalyze the reaction. By lowering the activation energy, such catalysts can increase the rate of a particular chemical reaction by several orders of magnitude. Applied in a commercial setting, catalysts can significantly reduce the costs associated with electricity-producing devices such as fuel cells.

Fuel cells are electrochemical devices that convert the chemical energy stored in fuels and oxygen into electricity and small molecule byproducts such as water and $CO_2$. Like conventional batteries, fuel cells possess both an anode and a cathode. Also like conventional batteries, fuel is oxidized and electrons are produced in the anode and in the cathode. An electrolyte connects the anode and cathode. Ionic current through the electrolyte completes the electrical circuit. A significant advantage of fuel cells over conventional batteries is that the former do not require recharging. Rather, fuel cells produce electricity by consuming a fuel such as hydrogen, reformate gas, or methanol.

Thus, machines powered by fuel cells offer flexibility not available in battery-powered machines. For example, like conventional internal combustion engine-powered motor vehicles, fuel cell-powered motor vehicles offer a long range of travel between refueling. Moreover, fuel cell-powered vehicles can be quickly "refueled" at conventional service stations. In comparison, conventional battery-powered vehicles suffer short travel ranges, a problem compounded by the relatively time-consuming recharging process.

Another advantage of fuel cells is that they are capable of providing energy in an efficient manner with relatively few adverse effects on the environment. For example, methanol fuel cells are attractive alternatives to internal combustion engines for mobile applications as they operate at lower noise levels, offer greater energy efficiency, and emit fewer pollutants and greenhouse gases. Likewise, hydrogen fuels cells or reformate gas fuel cells are also quiet, energy efficient, and less polluting than conventional internal combustion engines.

Despite their apparent advantages, fuel cells have not achieved widespread commercial application, in part because the materials used to catalyze the fuel cell reaction have not been optimized. For example, the materials conventionally used as catalysts suffer rapid poisoning (i.e., loss of catalytic activity caused by the fuel or byproducts of the reaction) and poor efficiency (i.e., high overpotentials are required to produce current). Thus, there exists a great need for new electrocatalytic materials that resist poisoning and catalyze the electricity-producing reaction efficiently.

Materials customarily used as anode or cathode electrocatalysts are pure metals or simple alloys (e.g., Pt, Pt/Ru, Pt/Ni) supported on high surface area carbon. For example, the state-of-the-art anode catalysts for hydrocarbon (e.g., methanol) fuel cells are based on platinum (Pt)-ruthenium (Ru) alloys. Heretofore, the best known catalyst was $Pt_{50}/Ru_{50}$ (numbers in subscript indicate atomic ratios). Gasteiger et al., *J Phys. Chem.*, 98:617, 1994; Watanabe et al., *J Electroanal. Chem.*, 229:395, 1987. Other binary alloys useful as anode catalysts include Pt/Sn, Pt/Mo, Pt/Os, and Pt/Re. More recently, ternary alloys of Pt/Ru/Os have been developed for use as anode catalysts. Ley et al., *J Electrochem. Soc.*, 144:1543, 1997; U.S. Patent No. 5,856,036. The benchmark cathode catalyst for methanol, hydrogen, and reformate gas fuel cells is pure elemental platinum supported on carbon (Pt/C) at a metal loading of 20–30% by weight. Still other materials for use as catalysts are known.

U.S. Pat. No. 4,880,711 to Luczak et al. teaches a ternary alloy catalyst for fuel cells comprising platinum and gallium, and additionally chromium, cobalt, nickel, and/or mixtures thereof. This alloy catalyst requires at least about 50% platinum to be an effective catalytic material. Other elements in the same periodic group, namely iridium, rhodium, osmium, and ruthenium, are indicated to be substitutable for a portion of the platinum.

U.S. Pat. No. 4,127,468 to Alfenaar et al. discloses a process for producing metal electrodes in which a basis-metal electrode comprising a basis-metal which is present in a finely divided or porous state, and which is selected from the group consisting of the noble metals from Groups IB, IIB, or VII of the Periodic Table of the Elements, or an alloy of at least one of said metals, is contacted with a solution containing an alloying element. The alloying element is selected from the group consisting of an element from Groups IIIA, IVA, VA, VIA, VII, IB, IIB, VIIB, or combinations thereof, of the Periodic Table of the Elements. The alloying-element compound is reduced in situ to form a free-alloying element, whereby the alloying element forms an alloy with the basis-metal. Preferred basis-metals include palladium, platinum, palladium-platinum, and platinum-iridium.

U.S. Pat. No. 5,208,207 to Stonehart et al. discloses an electrocatalyst comprising a ternary alloy essentially consisting of platinum-palladium-ruthenium supported on an inorganic support. U.S. Pat. No. 5,225,391 to Stonehart et al. teaches an electrocatalyst comprising a four-element alloy consisting essentially of platinum, nickel, cobalt, and manganese supported on an inorganic support. U.S. Pat. No. 5,286,580 to Ippommatsu et al. discloses a fuel electrode for a high temperature solid electrolyte fuel cell comprising ruthenium, osmium, rhodium or iridium, or an alloy thereof. U.S. Pat. No. 5,876,867 to Itoh et al. discloses an electrocatalyst comprising an alloy of platinum with a base metal selected from gallium, vanadium, chromium, manganese, iron, cobalt, nickel, and copper, the alloy being supported on a conductive carbon powder, the electrocatalyst having a structure of vacant lattice site type lattice defects.

SUMMARY OF THE INVENTION

The invention is based on the discovery of new, highly-efficient alloys for use as electrocatalysts in fuels cells.

Accordingly the invention features a catalyst for use in electrochemical reactor devices, the catalyst including an alloy consisting essentially of two or more metals selected from platinum, ruthenium, iridium, and osmium. The alloy can include three, four, or all five of these metals. In some embodiments, the catalyst is an anode including an alloy having platinum in an atomic percent greater than about 11 and less than about 44, and one or more other metals selected from rhodium, ruthenium, and iridium. In still other embodiments the anode includes an alloy that is $Rh_{56}Ru_{19}Ir_{13}Pt_{12}$, $Rh_{47}Pt_{27}Ru_{13}Ir_{13}$, $Pt_{58}Ru_{25}Rh_{17}$, $Pt_{45}Ir_{33}Rh_{27}$, $Pt_{44}Ru_{41}Os_{10}Ir_{5}$, $Pt_{47}Ru_{29}Os_{20}Ir_{4}$, and $Pt_{62}Rh_{25}Os_{13}$ (the subscription indicating atomic percentages).

The invention also features a catalyst that is a cathode including an alloy having rhodium in an atomic percent greater than about 11 and less than about 88, and one or more other metals selected from ruthenium, platinum, osmium, and iridium. Cathodes within the invention can include the alloys Pt(3.5)Ru(2)Os(2.5)Ir(1) and Rh(4)Pt(2.5)Ru(1.5)Ir(1). (Parenthetical numbers indicate atomic ratios).

Other catalysts within the invention include an alloy made from a mixture of two or more precursor metals, one of the precursor metals being molybdenum or a molybdenum salt. In some cases, this mixture also includes one or more metals selected from platinum, rhodium, ruthenium, iridium, and osmium. Also within the invention are catalysts including an alloy that is made from a mixture comprising two or more precursor metals and a reducing agent.

Additionally, catalysts within the invention can further include an inorganic support, such as a carbon support. Also featured in the invention are electrochemical reaction devices that include a catalyst of the invention. Such devices can be fuel cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
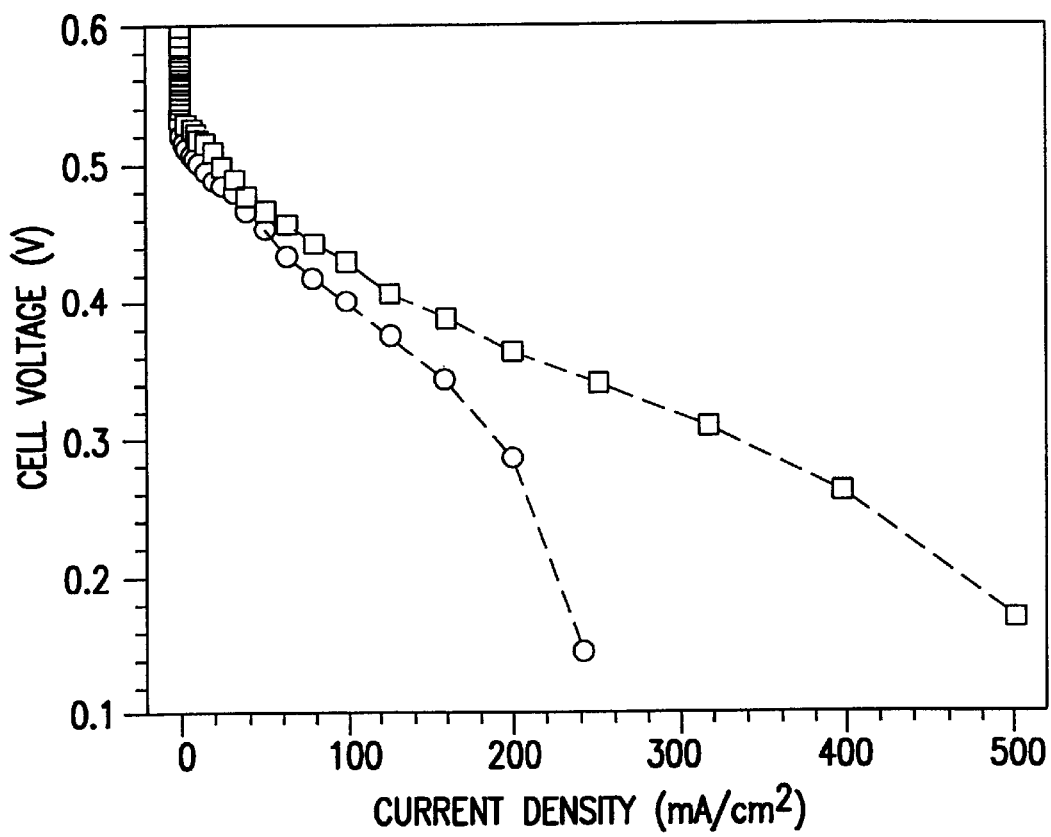
FIG. 1 is a graph depicting the steady-state current-voltage data for direct methanol fuel cells made from $Pt_{44}Ru_{41}Os_{10}Ir_{5}$ (open boxes) or $Pt_{50}Ru_{50}$ (open circles) anode electrocatalysts. Anode: 4.0 mg/cm$^2$, 12.5 mL/min methanol, 0.5 M, 0 psig; cathode: 4.0 mg/cm$^2$ Pt, 400 SCCM dry air @10 psig; cell 60° C., Nafion 117. Cell potentials were compensated for series resistance.

The invention is based on the discovery of new alloys that can be used as highly efficient electrodes in fuel cells.

Compositions for use as Anodes and Cathodes

Some alloys made up of a mixture of metals selected from platinum, rhodium, ruthenium, iridium, and osmium serve as efficient electrodes by catalyzing a fuel cell reaction. Using a combinatorial chemistry-based technique, thousands of different metal alloys based on two or more of the aforementioned metals were prepared and then screened for the ability to catalyze the oxidation reaction (for anode materials) or the reduction action (for cathode materials) in a fuel cell. Using this technique a large number of alloy compositions useful in anodes and cathodes was identified. Some of these performed significantly better than conventional electrode materials. Specific alloys within the invention are described in the drawings and the Examples set forth below. Also within the invention are alloys that comprise elements in about the same atomic percent or atomic ration of those specifically disclosed in the drawings and Examples, it being appreciated that alloys comprising the same elements in about but not exactly the same would have electrocatalytic ability about (slightly better or worse) the same as the specifically disclosed alloys. For example, referring to the compositional tetrahedral maps described below, it can be appreciated that alloys falling into areas bound by or near those of active catalysts would likewise have similar electrocatalytic activity. Thus, those compounds are within the invention. For instance, $Pt_{22}Ru_{44}Ir_{22}Os_{11}$, and $Pt_{22}Ru_{44}Ir_{11}O_{22}$ are specifically disclosed. Therefore, $Pt_{22}Ru_{44}Ir_{21}O_{12}$, $Pt_{22}Ru_{44}Ir_{20}Os_{13}$, $Pt_{22}Ru_{44}Ir_{19}Os_{14}$, ect. and $Pt_{22}Ru_{44}Ir_{21.5}O_{11.5}$, $Pt_{22}Ru_{44}Ir_{21.55}Os_{11.45}$ and the like are within the invention.

While the alloys of the invention can be used in a homogeneous, solid, non-particulate form, in preferred embodiments, to increase the surface area of the alloy in contact with the fuel cell reactants, the alloys are used in a particulate and/or porous form. Particles of the alloys can be made according to methods known in the art. E. g., U.S. Pat. No. 5,208,207. For example, a reducing agent can be added to a mixture of metal salts to form particulate metal alloys. Alternatively or additionally, metal alloys can be coated or otherwise applied onto a particulate support. E. g., U.S. Pat. No. 5,759,944. This support can be any compatible substance, such as a particulate inorganic oxide (e.g., silica and alumina) or carbon (e.g., graphite). Preferably, the support used is high surface area carbon at a metal loading of between 20–30%.

As an example, metal alloys coated on carbon are formed by first adding an aqueous solution of carbon support to a solution of metal alloy formed by addition of a reducing agent to an aqueous metal ion solution. This solution is then agitated (e.g., by a supersonic wave agitator) to form a slurry. The slurry is then placed in a hot (e.g., 75–80° C.) oven for 1 to 3 days to yield a dry powder. This dry powder can be washed to remove reaction by-products with, for example, distilled water. Other methods and variations of the foregoing are known in the art.

Preparation of Electrocatalysts

Metal alloys for use as catalysts in the invention can be prepared according to methods known in the art. In a preferred method, the metal alloy catalysts within the invention are prepared from the corresponding metal salts by mixing the desired salts together in the appropriate molar ratio in an aqueous solution, and then adding a chemical reducing agent to form the alloy. See, e.g., McKee, D. W., and Norton, F. J., *Journal of Catalysis*, 3:252, 1964; and McKee, D. W., *Journal of Catalysis*, 14:355, 1969. Suitable chemical reducing agents include borohydride, hydrogen gas, formaldehyde, hydroxylamine, and hydrazine. The alloy particles thus formed can be analyzed by common analytical techniques, such as electron microscopy and X-ray diffraction analysis, to monitor the degree of metal mixing and the relative crystalline quality of alloys. The atomic ratio of the metals comprising the alloy can be altered by simply varying the quantity of each metal salt added to the mixture.

For example, various electrocatalysts of the invention were prepared by dispensing precursor inks containing the appropriate metal salts (e.g., $H_2PtCl_6$, $RuCl_3$, $Na_2MoO_4$, $RhCl_3$, $K_2IrCl_6$, and $OsCl_3$) dissolved in an aqueous solution (e.g., water, or a glycerol/water mixture) onto a Toray carbon support. Inks were delivered in such a way (e.g., with a microliter syringe or using an ink jet printer) and in such a quantity that each printed spot on the support contained a preselected number of moles of metal prior to the reduction step. The printed metal mixtures were reduced with a 40-fold molar excess of aqueous sodium borohydride and then washed with water. Specific catalysts were also made in bulk according to the same process by simply scaling up the quantities of reactants employed and using macroscale equipment (e.g., standard pipets and glassware rather than micropipets and printers). Analysis of the borohydride reduction of the metal salts followed by washing with neutral water showed that, with the exception of Mo, the elemental metals are quantitatively retained in the formed alloys. Little or no Mo was retained in the alloys.

Still other methods are known for preparing the catalysts of the invention. Commonly used methods include electrochemical reduction of metal salt mixtures, arc-melting, annealing metal colloids, vapor phase deposition, and electroplating. Electrochemical reduction of metal salt mixtures is achieved similarly to the above-described chemical reduction method, except an electrochemical reducing forced is applied to the metal salt mixture, rather than a chemical reducing agent. In a variation of the electrochemical and chemical reduction methods, a mixture of metal oxides in colloidal form (i.e., from a mixture of colloidal suspensions) is prepared and then reduced electrochemically or chemically to form a metal alloy. In another method, a mixture of finely divided metals or metal colloids is annealed to form an alloy. Vapor phase deposition (e.g., by evaporation, sputtering, or chemical vapor deposition) can be used to form alloys by methods known in the art. In one variation of this method, the various metals are deposited one at a time to make a layered film. The resultant film is then annealed to make the corresponding metal alloy.

In many of the above methods, the atomic ratio of the metals comprising the alloy can be altered by simply varying the quantity of each elemental metal added to the mixture to be reacted. For instance, equal molar quantities of Pt and Ru (metal, metal oxides, metal salts, or metal colloids) are added together before the alloying reaction to form a platinum-ruthenium alloy where the atomic ratio of platinum to ruthenium is 1:1 (i.e., $Pt_1Ru_1$), or 50:50 (i.e., $Pt_{50}Ru_{50}$) when expressed as atomic percent. As a further illustration of this method, if an alloy having an atomic ratio of Pt to Ru of 3:1 is desired, three moles of Pt are added to every one mole of Ru. In this manner alloys comprising two or more metals in a specific atomic ratio can be prepared.

Testing the Catalytic Activity of Electrode Compositions

Electrocatalytic activity of compositions is typically assessed by making a direct measurement of one or more electrochemical parameters. As one example, current can be measured as a function of potential by, for instance, applying a potential to an individual electrode in an electrochemical reaction device and measuring the current generated. The current produced at a given potential is greater with efficient electrocatalysts than with inefficient electrocatalysts.

Indirect methods of measuring electrocatalytic activity of the compositions are also known. E. g., Reddington et al, *Science*, 280:267 (1998). For example, measurement of the pH in the area immediately proximal to an electrode composition in an electrochemical reaction device can be used to estimate that composition's catalytic activity because the oxidation and reduction reactions that take place in fuel cells result in the production and consumption of protons, respectively. Compositions that perform most efficiently produce the greatest pH change at the lowest applied potential. That is, compositions that are more efficient at catalyzing oxidation reactions (i.e., better anode catalysts) exhibit a more acidic pH in the area immediately surrounding the electrode at a given applied potential than less efficient compositions. Similarly, compositions that are more efficient at catalyzing reduction reactions (i.e., better cathode catalysts) exhibit a more alkaline pH in the area immediately surrounding the electrode at a given applied potential than less efficient compositions. Methods of measuring pH are well known in the art and include, for example, use of pH meters, uses of pH paper, and use of fluorescent pH indicators (e.g., quinine, acridine, $Ni^+$ complexed with 3-pyridin-2-yl-<4,5,6>triazolo-<1,5-a >pyridine (Ni-PTP), Eosin Y, Phloxine B, etc.)

EXAMPLES

Example 1

Compositions for Fuel Cell Anode Catalysts

Compositions were prepared and tested according to the method described in Reddington et al., *Science*, 280:1735, 1998. Electrode arrays were prepared in duplicate by printing precursor inks containing salts of the indicated metal (e.g., $H_2PtCl_6$, $RuCl_3$, $Na_2MoO_4$, $RhCl_3$, $K_2IrCl_6$, and $OsCl_3$) dissolved in glycerol/water onto a Toray carbon support. Inks were delivered so that each spot in the array contained the same total number of moles of metal prior to the reduction step using an ink jet printer (e.g., an Apple Color Stylewriter2500 where the pattern for each ink was drawn in grayscale with commercial drawing software). The spots were reduced with a forty-fold molar excess of sodium borohydride, and the arrays were washed repeatedly with deionized water.

The array then served as the working electrode in a three-electrode cell. The electrode array contacted an electrolyte solution maintained at pH 3 and contained Ni-PTP and methanol. After conditioning the array for several minutes, the potential was gradually increased from −150 mV vs. DHE (dynamic hydrogen reference electrode) until visible fluorescence was observed. Bulk catalysts (used in B below) were prepared in a similar way, except that the solutions of metal salts were prepared by standard volumetric methods rather than by delivery from an ink-jet printer (e.g., the appropriate quantities of metal salts were dissolved in water to an overall concentration of 2 mM, pH adjusted to 9; a ten-fold excess of 5% wt % sodium borohydride was added one drop at a time; the precipitate washed ten times with water; and dried at 110° C.).

The solid catalysts were tested unsupported at loadings of 0.4–1.2 mg/cm$^2$ in the same fuel mixture and on Toray carbon, in a equipped with a DHE and Pt counterelectrode. Current-voltage curves were recorded after an initial conditioning period, during which all catalysts lost some activity, presumably because of poisoning. The most active catalysts were also tested in direct methanol fuel cells. The corresponding curves are shown in FIG. 1.

A. Precursor Compositions (in atomic percent) Used to Form Alloys with Catalytic Activity Precursor compositions were printed onto Toray carbon arrays in the atomic percent indicated below using the method described above. The arrays were prepared and installed as the working electrode in a three-electrode cell, and then tested for catalytic efficiency according to the above described method. The data obtained is expressed in three-dimensional tetrahedral diagrams shown in FIGS. 3 and 4. The spheres in the diagrams each correspond to each particular metal composition tested. In the quaternary maps, the spheres at each vertex represent compositions 100% (99/99) of the element indicated. Spheres removed one space away from a vertex along a binary edge represent alloys composed 88/99 of the element indicated at the proximal vertex, and 11/99 of the element indicated at the distal vertex located at the other end of the binary edge. In the same manner, spheres removed two spaces from a vertex along a binary edge represent alloys having 77/99 of the element indicated at the proximal vertex and 22/99 of the element indicated at the distal vertex. This pattern continues in 11/99 increments along the binary edge. Thus, spheres located at the vertices represent pure metal and the sphere located in between the vertices along the binary edge represent binary alloys.

The same geometrical pattern continues in the other portions of the tetrahedron. Thus, spheres located on each outer triangular surface of the tetrahedron (except those on the binary edge) represent ternary alloys formed by the three elements indicated at the vertices of the triangle. Similarly, those spheres located in the interior of the tetrahedron represent quaternary alloys. The specific atomic ratios of each element in an alloy represented by a particular sphere can thus be calculated according to its placement in the tetrahedron. For pentanary alloys, the tetrahedral pattern is expanded into four dimensions by plotting a series of tetrahedrons, each of the tetrahedrons representing alloys with varying concentrations of the fifth element. In these maps, composition atomic percents range from 11–55%, in 11 atomic percent increments. See FIGS. 3 and 4 for examples.

Compositions that were tested included alloys prepared from the metals listed below wherein the each metal was added at between 0–99 atomic percent in 11 percent increments. To facilitate preparation and testing of the arrays, the indicated 99 atomic percent is actually 100 percent of that metal. Likewise, the indicated 11 atomic percent is actually 11/99 that metal, 22 atomic percent is 22/99 that metal, and so on.

B. Other Compositions (subscript=atomic percent) Used to Form Alloys With High Catalytic Activity Alloys were prepared in bulk or in an array as described above and tested for current-voltage (e.g., amps generated per volts applied) in a methanol fuel cell or for proton concentration by the method described above (i.e., in a gas diffusion cell using the Ni—PTP probe). Each of the compositions below functioned efficiently as anode catalysts. Results from the testing of the first-listed composition are shown in FIG. 1.

1. $Pt_{44}Ru_{41}Os_{10}Ir_5$
2. $Pt_{47}Ru_{29}Os_{20}Ir_4$ (results not shown)
3. $Pt_{62}Rh_{25}Os_{13}$ (results not shown)

Example 2

Compositions for Fuel Cell Cathode Catalysts

A. Compositions (in atomic percent) Used to Form Alloys with Catalytic Activity The following compositions were prepared and printed onto Toray carbon arrays as described in Example 1. The back of the array was made hydrophobic by a Teflon® coating, and the array then served as the working electrode in a three-electrode gas diffusion cell. Oxygen was diffused through the carbon to simulate the kind of gas diffusion cathode environment found in a typical polymer electrolyte membrane (PEM) cell. The potential of the array was made progressively more negative, starting from a potential at which oxygen is not easily reduced. Phloxine B (active at basic pH's) was used as the fluorescent indicator dye to indicate active catalytic compositions. Compositions that were tested included alloys prepared from the metals listed below wherein each metal was added at between 0–99 atomic percent in 11 percent increments. The catalytic activity of the compositions is shown in the tetrahedral composition maps shown in FIG. 4. The elemental compositions of active alloy catalysts (i.e., those that generated a visible fluorescent signal) were extrapolated from FIG. 2 and are indicated below (numbers indicate atomic percent as described in Example 1).

| Pt | Ru | Rh | Ir | Os |
|----|----|----|----|----|
| 66 | 11 | — | 11 | 11 |
| 55 | 22 | — | 11 | 11 |
| 55 | 11 | — | 11 | 22 |
| 44 | 55 | — | — | — |
| 44 | 33 | — | 11 | 11 |
| 44 | 22 | — | 11 | 11 |
| 44 | 11 | — | 22 | 22 |

-continued

| Pt | Ru | Rh | Ir | Os |
|---|---|---|---|---|
| 33 | 66 | — | — | — |
| 33 | 33 | — | 11 | 22 |
| 22 | 44 | — | 11 | 22 |
| 33 | 22 | 33 | 11 | — |
| 33 | 11 | 44 | 11 | — |
| 22 | 77 | — | — | — |
| 22 | 55 | — | 22 | — |
| 22 | 22 | 44 | 11 | — |
| 22 | 11 | 55 | 11 | — |
| 22 | 11 | 44 | 22 | — |
| 11 | 88 | — | — | — |
| 11 | 66 | — | 22 | — |
| 11 | 55 | — | 33 | — |
| 11 | 11 | 55 | 22 | — |
| — | 33 | 11 | 44 | 11 |
| — | 33 | 11 | 33 | 22 |
| — | 33 | 11 | 22 | 33 |
| — | 22 | 11 | 44 | 22 |
| — | 22 | 11 | 33 | 33 |
| — | 11 | 11 | 44 | 33 |
| — | 11 | 11 | 33 | 44 |
| — | 11 | 11 | 22 | 55 |
| 44 | 33 | 11 | — | 11 |
| 44 | 22 | 22 | — | 11 |
| 44 | 11 | 33 | — | 11 |
| 33 | 44 | 11 | — | 11 |
| 33 | 33 | 22 | — | 11 |
| 33 | 33 | 11 | — | 22 |
| 33 | 22 | 33 | — | 11 |
| 33 | 22 | 22 | — | 22 |
| 33 | 11 | 44 | — | 11 |
| 22 | 22 | 22 | — | 33 |
| 22 | 55 | 11 | — | 11 |
| 22 | 44 | 22 | — | 11 |
| 22 | 44 | 11 | — | 22 |
| 22 | 33 | 33 | — | 11 |
| 22 | 33 | 22 | — | 22 |
| 22 | 33 | 11 | — | 33 |
| 22 | 22 | 44 | — | 11 |
| 22 | 22 | 33 | — | 22 |
| 22 | 11 | 55 | — | 11 |
| 11 | 22 | 33 | — | 33 |
| 11 | 11 | 66 | — | 11 |
| 11 | 22 | 66 | — | — |
| 11 | 33 | 44 | — | — |
| — | 22 | 44 | — | 33 |
| — | 11 | 44 | — | 44 |
| 11 | 55 | 33 | — | — |
| 22 | 44 | 33 | — | — |
| 33 | 33 | 33 | — | — |
| 44 | 22 | 33 | — | — |
| 33 | 11 | 33 | — | 22 |
| 22 | 11 | 33 | — | 33 |
| 55 | 11 | 22 | — | 11 |
| 44 | 11 | 22 | — | 22 |
| 33 | 11 | 22 | — | 33 |
| 22 | 11 | 22 | — | 44 |
| 55 | 22 | 11 | — | 11 |
| 44 | 22 | 11 | — | 22 |
| 33 | 22 | 11 | — | 33 |
| 22 | 22 | 11 | — | 44 |
| 66 | 11 | 11 | — | 11 |
| 55 | 11 | 11 | — | 22 |
| 44 | 11 | 11 | — | 33 |
| 11 | 88 | — | — | — |
| 22 | 77 | — | — | — |
| 33 | 66 | — | — | — |
| 44 | 55 | — | — | — |
| 11 | 11 | 66 | 11 | — |
| 11 | 33 | 55 | — | — |
| 22 | 22 | 55 | — | — |
| 11 | 22 | 55 | 11 | — |
| 11 | 44 | 44 | — | — |
| 22 | 33 | 44 | — | — |
| 33 | 22 | 44 | — | — |
| 11 | 55 | 33 | — | — |
| 22 | 44 | 33 | — | — |

-continued

| Pt | Ru | Rh | Ir | Os |
|---|---|---|---|---|
| 33 | 33 | 33 | — | — |
| 22 | 33 | 33 | 11 | — |
| 44 | 22 | 33 | — | — |
| 22 | 44 | 22 | 11 | — |
| 33 | 33 | 22 | 11 | — |
| 22 | 55 | 11 | 11 | — |
| 33 | 44 | 11 | 11 | — |
| 11 | 88 | — | — | — |
| 22 | 77 | — | — | — |
| 33 | 66 | — | — | — |
| 22 | 66 | — | 11 | — |
| 11 | 66 | — | 22 | — |
| 44 | 55 | — | — | — |
| 33 | 55 | — | 11 | — |
| 22 | 55 | — | 22 | — |
| 11 | 55 | — | 33 | — |
| 44 | 11 | 11 | 22 | 11 |
| 22 | 22 | 22 | 11 | 22 |
| 22 | 11 | 44 | 11 | 11 |
| 22 | 11 | 33 | 11 | 22 |
| 22 | 22 | 11 | 11 | 33 |
| 22 | 11 | 11 | 11 | 44 |
| 22 | 11 | 22 | 33 | 11 |
| 11 | 11 | 55 | 11 | 11 |
| 11 | 22 | 44 | 11 | 11 |
| 11 | 33 | 33 | 11 | 11 |
| 11 | 22 | 33 | 11 | 22 |
| 11 | 11 | 33 | 11 | 33 |
| 11 | 44 | 22 | 11 | 11 |
| 11 | 33 | 22 | 11 | 22 |
| 11 | 22 | 22 | 11 | 33 |
| 11 | 55 | 11 | 11 | 11 |
| 11 | 22 | 11 | 11 | 44 |
| 11 | 11 | 11 | 11 | 55 |
| 11 | 11 | 44 | 22 | 11 |
| 11 | 22 | 33 | 22 | 11 |
| 11 | 33 | 22 | 22 | 11 |
| 11 | 44 | 11 | 22 | 11 |
| 11 | 11 | 11 | 55 | 11 |

B. High Catalytic Activity Alloys (parenthetical numbers correspond to atomic ratio)

Figure 2:
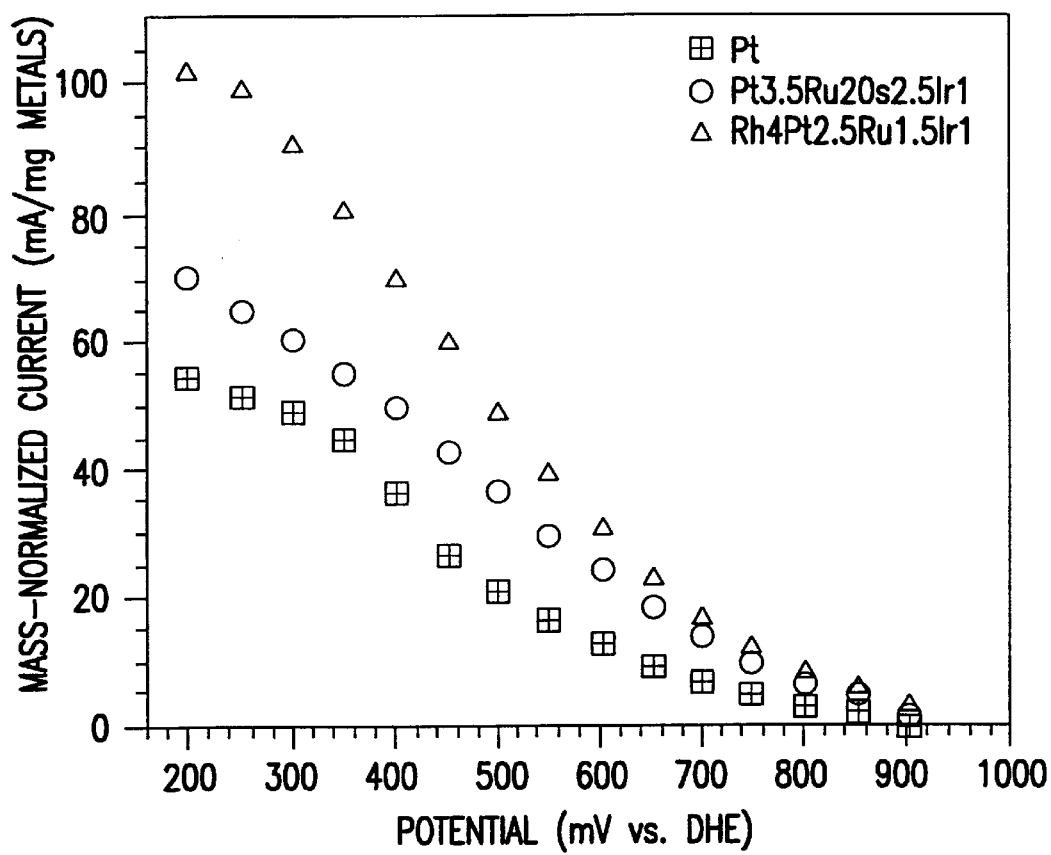
FIG. 2 is graph depicting cathode polarization curves for the indicated cathodes (30% metals, supported on Vulcan XC-72 carbon). Data using Pt cathodes are shown using hatched boxes, data using $Rh_{[4]}Pt_{[2.5]}Ru_{[1.5]}Ir_{[1]}$ cathodes (bracketed numbers=atomic ratio) are shown in solid triangles, and data using $Pt_{[3.5]}Ru_{[2]}Os_{[2.5]}Ir_{[1]}$ cathodes (bracketed numbers=atomic ratio) are shown in open circles. Measurements were obtained in a gas diffusion cell where the electrode area was approximately 1 cm$^2$, and oxygen was introduced from the back of the Teflon®-coated Toray carbon working electrode at a pressure of 1 atm.

Bulk catalysts were prepared as described in Example 1 and tested for catalytic activity in a gas diffusion cell. Test electrodes were prepared at 30% metal loading on Vulcan XC-72 carbon. The electrode area was approximately 1 cm². Oxygen was introduced through the Teflon®-coated Toray carbon working electrode backing at a pressure of 1 atm and the other side of the electrode contacted a sulfuric acid solution containing the reference and counter electrodes. The following alloys were substantially more active than Pt prepared by the same method and on the same support. Results are shown in FIG. 2.

1. Rh(4)Pt(2.5)Ru(1.5)Ir(1)
2. Pt(3.5)Ru(2)Os(2.5)Ir(1)

Example 3

Compositions for Fuel Cell Cathode (Oxygen reduction) Catalysts

Figure 3:
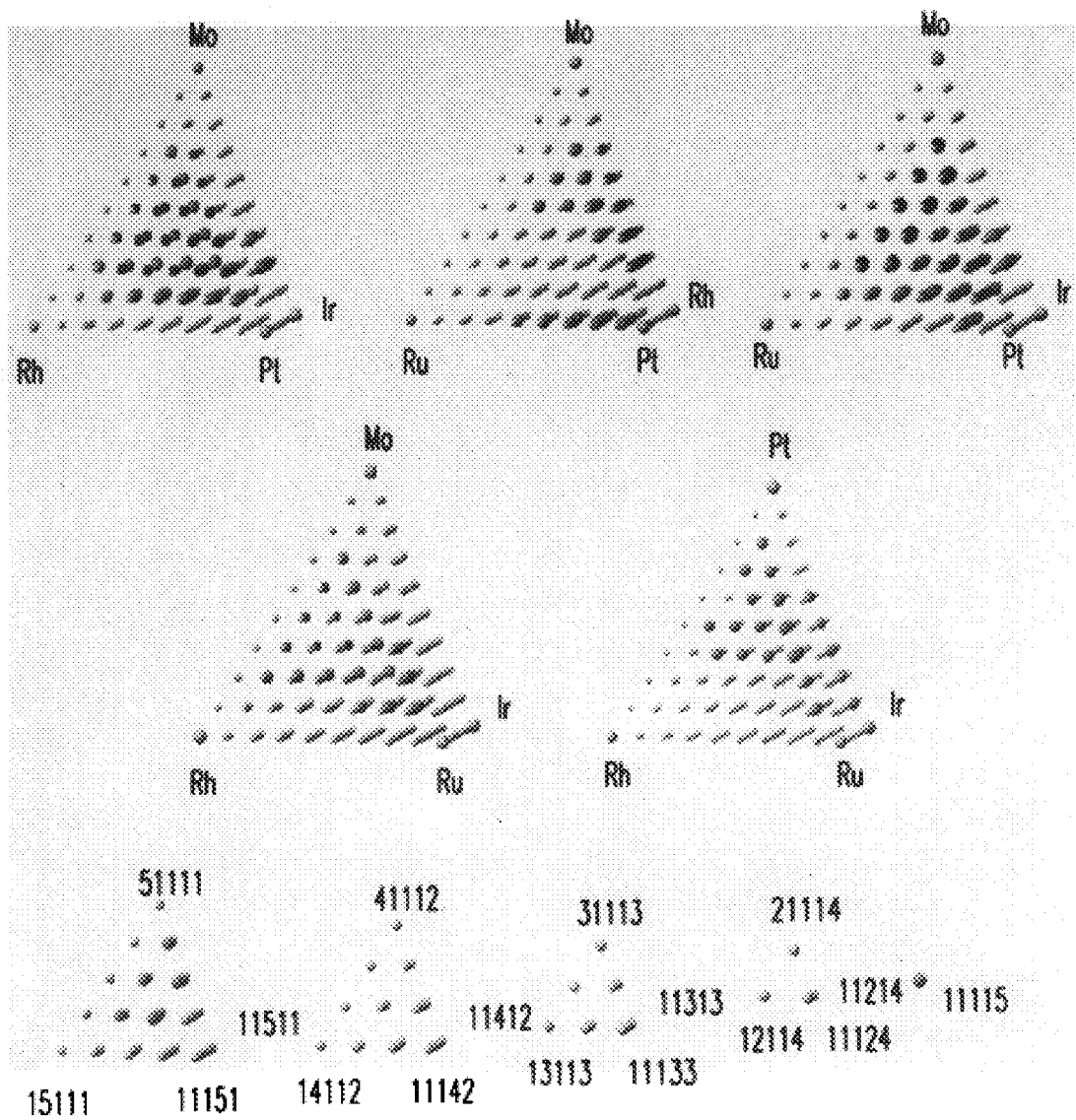
FIG. 3 shows quaternary and pentanary precursor composition maps for unsupported Mo-Pt-Ru-Rh-Ir compositions that manifest zones of high activity as oxygen electroreduction catalysts, as determined by optical screening. In the pentanary map, Ir content increases progressively (11, 22, 33, 44, and 55 atomic percent) from left to right. Larger or darker spots indicate regions of higher activity.
Figure 4:
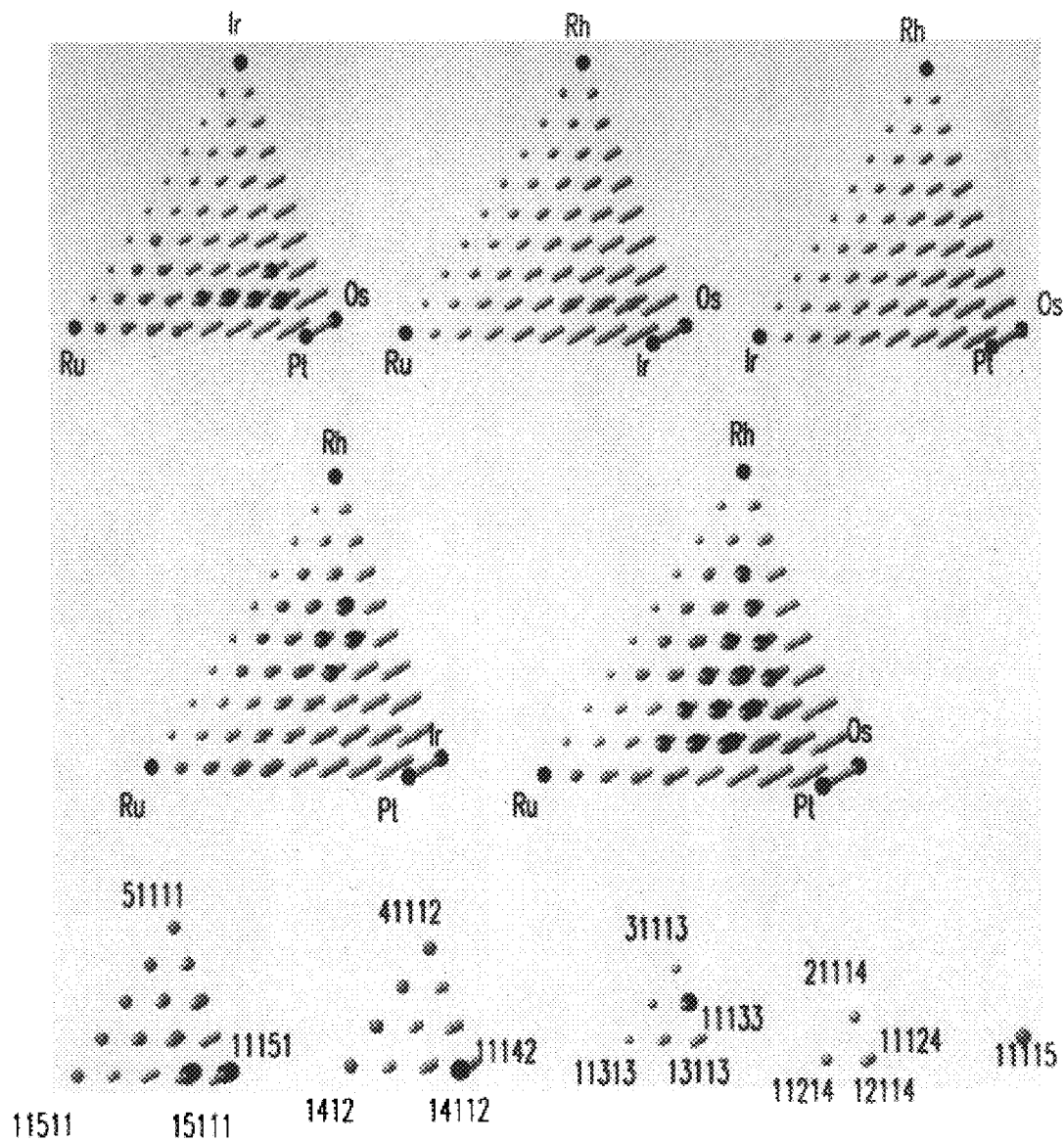
FIG. 4 shows quaternary and pentanary precursor composition maps for carbon-supported Rh-Pt-Ru-Os-Ir compositions that manifest zones of high activity as oxygen electroreduction catalysts, as determined by optical screening. In the pentanary map, Ir content increases progressively (11, 22, 33, 44, and 55 atomic percent) from left to right. Larger or darker spots indicate regions of higher activity.

Compositions (in atomic percent) used to form alloys with catalytic activity were prepared in the presence of carbon support material and printed in arrays onto Toray carbon as described in Example 1. The compositions were tested for catalytic ability using the same method described in Example 2. Compositions that were tested included alloys prepared from the metals listed below wherein each metal was added at between 0–99 atomic percent in 11 percent increments. The results are shown in FIG. 3. Active catalysts (i.e., those that generated a visible fluorescent signal) are also indicated below (numbers indicate atomic percent as described in Example 1).

| Mo | Rh | Pt | Ir | Ru |
|----|----|----|----|----|
| 66 | 22 | — | 22 | — |
| 66 | 11 | 22 | — | — |
| 55 | 33 | — | 11 | — |
| 55 | 22 | 22 | — | — |
| 55 | 22 | — | 22 | — |
| 55 | 11 | 33 | — | — |
| 44 | 44 | 11 | — | — |
| 44 | 33 | 22 | — | — |
| 44 | 33 | — | 22 | — |
| 44 | 22 | 33 | — | — |
| 44 | 22 | — | 33 | — |
| 44 | 11 | 44 | — | — |
| 33 | 55 | — | 11 | — |
| 33 | 44 | — | 22 | — |
| 33 | 44 | 22 | — | — |
| 33 | 33 | — | 33 | — |
| 33 | 33 | 33 | — | — |
| 33 | 22 | 44 | — | — |
| 33 | 22 | 33 | 11 | — |
| 33 | 22 | — | 44 | — |
| 33 | 11 | 44 | 11 | — |
| 33 | — | 22 | 44 | — |
| 33 | — | 33 | 33 | — |
| 33 | 11 | 55 | — | — |
| 22 | 55 | 22 | — | — |
| 22 | 44 | 33 | — | — |
| 22 | 33 | 44 | — | — |
| 22 | 22 | 55 | — | — |
| 22 | 11 | 66 | — | — |
| 33 | 55 | 11 | — | — |
| 22 | 66 | 11 | — | — |
| 22 | 66 | — | 11 | — |
| 22 | 55 | — | 22 | — |
| 22 | 44 | — | 33 | — |
| 22 | 33 | — | 44 | — |
| 22 | 22 | 44 | 11 | — |
| 22 | 22 | — | 55 | — |
| 22 | 11 | 55 | 11 | — |
| 22 | 11 | 44 | 22 | — |
| 22 | — | 44 | 33 | — |
| 22 | — | 33 | 44 | — |
| 22 | — | 22 | 55 | — |
| 11 | 66 | 11 | 11 | — |
| 11 | 55 | 22 | 11 | — |
| 11 | 55 | 11 | 22 | — |
| 11 | 44 | 11 | 33 | — |
| 11 | 44 | 33 | 11 | — |
| 11 | 33 | 22 | 33 | — |
| 11 | 33 | 33 | 22 | — |
| 11 | 33 | 44 | 11 | — |
| 11 | 22 | 33 | 33 | — |
| 11 | 22 | 44 | 22 | — |
| 11 | 22 | 55 | 11 | — |
| 11 | 22 | 55 | 11 | — |
| 11 | 11 | 44 | 33 | — |
| 11 | 11 | 55 | 22 | — |
| 11 | 11 | 66 | 11 | — |
| 66 | 11 | 22 | — | — |
| 66 | 11 | 11 | — | 11 |
| 55 | 11 | 33 | — | — |
| 55 | 11 | 11 | — | 22 |
| 55 | 22 | 11 | — | 11 |
| 55 | 11 | 22 | — | 11 |
| 55 | 22 | 22 | — | — |
| 44 | 11 | 44 | — | — |
| 44 | 11 | 11 | — | 33 |
| 44 | 22 | 11 | — | 22 |
| 44 | 11 | 33 | — | 11 |
| 44 | 22 | 22 | — | 11 |
| 44 | 22 | 33 | — | — |
| 44 | 33 | 11 | — | 11 |
| 44 | 33 | 22 | — | — |
| 33 | 11 | 55 | — | — |
| 33 | 11 | 44 | — | 11 |
| 33 | 22 | 33 | — | 11 |
| 33 | 22 | 44 | — | — |
| 33 | 33 | 33 | — | — |
| 33 | 44 | 22 | — | — |
| 33 | 55 | 11 | — | — |
| 22 | 11 | 66 | — | — |
| 22 | 22 | 55 | — | — |
| 22 | 33 | 44 | — | — |
| 22 | 44 | 33 | — | — |
| 22 | 55 | 22 | — | — |
| 22 | 66 | 11 | — | — |
| — | 11 | 33 | — | 55 |
| — | 11 | 44 | — | 44 |
| — | 22 | 33 | — | 44 |
| — | 11 | 55 | — | 33 |
| — | 22 | 44 | — | 33 |
| — | 33 | 33 | — | 33 |
| — | 11 | 66 | — | 22 |
| — | 22 | 55 | — | 22 |
| — | 33 | 44 | — | 22 |
| — | 11 | 77 | — | 11 |
| — | 22 | 66 | — | 11 |
| — | 33 | 55 | — | 11 |
| 66 | — | 11 | 11 | 11 |
| 55 | — | 11 | 11 | 22 |
| 55 | — | 22 | 11 | 11 |
| 55 | — | 11 | 22 | 11 |
| 55 | — | — | 33 | 11 |
| 44 | — | 11 | 11 | 33 |
| 44 | — | 22 | 11 | 22 |
| 44 | — | 11 | 22 | 22 |
| 44 | — | — | 33 | 22 |
| 44 | — | 33 | 11 | 11 |
| 44 | — | 11 | 33 | 11 |
| 44 | — | 22 | 22 | 11 |
| 33 | — | 11 | 11 | 44 |
| 33 | — | 22 | 11 | 33 |
| 33 | — | 11 | 22 | 33 |
| 33 | — | — | 33 | 33 |
| 33 | — | 33 | 11 | 22 |
| 33 | — | 22 | 22 | 22 |
| 33 | — | 11 | 33 | 22 |
| 33 | — | 44 | 11 | 11 |
| 33 | — | 33 | 22 | 11 |
| 33 | — | 22 | 33 | 11 |
| 33 | — | 11 | 44 | 11 |
| 33 | — | 55 | 11 | — |
| 33 | — | 44 | 22 | — |
| 33 | — | 33 | 33 | — |
| 22 | — | 11 | 11 | 55 |
| 22 | — | 11 | 22 | 44 |
| 22 | — | 22 | 11 | 44 |
| 22 | — | 33 | 11 | 33 |
| 22 | — | 22 | 22 | 33 |
| 22 | — | 11 | 33 | 33 |
| 22 | — | 44 | 11 | 22 |
| 22 | — | 33 | 22 | 22 |
| 22 | — | 22 | 33 | 22 |
| 22 | — | 11 | 44 | 22 |
| 22 | — | 55 | 11 | 11 |
| 22 | — | 44 | 22 | 11 |
| 22 | — | 33 | 33 | 11 |
| 22 | — | 44 | 33 | — |
| 22 | — | 33 | 44 | — |
| 22 | — | 22 | 44 | 11 |
| 22 | — | 11 | 55 | 11 |
| 11 | — | 44 | 11 | 33 |
| 11 | — | 55 | 11 | 22 |
| 11 | — | 44 | 22 | 22 |
| 11 | — | 66 | 11 | 11 |
| 11 | — | 55 | 22 | 11 |
| 11 | — | 44 | 33 | 11 |
| 11 | — | 11 | 11 | 66 |
| 11 | — | 11 | 22 | 55 |
| 11 | — | 22 | 11 | 55 |

-continued

| Mo | Rh | Pt | Ir | Ru |
|---|---|---|---|---|
| 11 | — | 33 | 11 | 44 |
| 11 | — | 22 | 22 | 44 |
| 11 | — | 11 | 33 | 44 |
| 11 | — | 33 | 22 | 33 |
| 11 | — | 22 | 33 | 33 |
| 11 | — | 11 | 44 | 33 |
| 11 | — | 33 | 33 | 22 |
| 11 | — | 22 | 44 | 22 |
| 11 | — | 11 | 55 | 22 |
| 11 | — | 22 | 55 | 11 |
| 11 | — | 11 | 66 | 11 |
| — | — | 55 | 22 | 22 |
| — | — | 44 | 33 | 22 |
| — | — | 33 | 44 | 22 |
| — | — | 22 | 55 | 22 |
| 66 | 22 | — | 11 | — |
| 55 | 22 | — | 22 | — |
| 44 | 44 | — | 11 | — |
| 44 | 22 | — | 33 | — |
| 33 | 22 | — | 33 | — |
| 33 | 11 | — | 22 | 33 |
| 22 | 66 | — | 11 | — |
| 22 | 55 | — | 22 | — |
| 22 | 44 | — | 33 | — |
| 22 | 33 | — | 44 | — |
| 22 | 22 | — | 55 | — |
| 22 | 11 | — | 22 | 44 |
| 22 | 11 | — | 33 | 33 |
| 11 | 33 | — | 22 | 33 |
| 11 | 22 | — | 22 | 44 |
| 11 | 22 | — | 33 | 33 |
| 11 | 11 | — | 22 | 55 |
| 11 | 11 | — | 33 | 44 |
| 11 | 11 | — | 44 | 33 |
| — | 11 | 77 | — | 11 |
| — | 22 | 66 | — | 11 |
| — | 11 | 66 | — | 22 |
| — | 22 | 55 | — | 22 |
| — | 11 | 55 | — | 33 |
| — | 11 | 55 | 11 | 22 |
| — | — | 55 | 22 | 22 |
| — | 44 | 44 | — | 11 |
| — | 33 | 44 | — | 22 |
| — | 22 | 44 | — | 33 |
| — | 11 | 44 | — | 44 |
| — | 11 | 44 | 11 | 33 |
| — | — | 44 | 33 | 22 |
| — | 44 | 33 | — | 22 |
| — | 33 | 33 | — | 33 |
| — | 22 | 33 | — | 44 |
| — | 11 | 33 | — | 55 |
| — | 11 | 33 | 11 | 44 |
| — | — | 33 | 44 | 22 |
| — | 11 | 22 | 22 | 44 |
| — | — | 22 | 55 | 22 |
| — | 11 | 11 | 55 | 22 |
| — | 11 | 11 | 44 | 33 |
| — | — | 11 | 22 | 66 |
| 44 | 22 | 11 | 11 | 11 |
| 33 | 22 | 22 | 11 | 11 |
| 33 | 33 | 11 | 11 | 11 |
| 33 | 22 | 11 | 11 | 22 |
| 22 | 22 | 33 | 11 | 11 |
| 22 | 33 | 22 | 11 | 11 |
| 22 | 22 | 22 | 11 | 22 |
| 11 | 11 | 11 | 55 | 11 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A catalyst for use in an electrochemical reactor device, said catalyst comprising an alloy comprising a first metal selected from the group consisting of platinum and ruthenium, and at least two additional metals selected from the group consisting of rhodium, iridium, and osmium.

2. A catalyst for use in an electrochemical reactor device, said catalyst comprising an alloy that comprises at least four different metals, said metals being selected from the group consisting of platinum, rhodium, ruthenium, iridium, and osmium.

3. The catalyst of claim 2, wherein said alloy comprises platinum, rhodium, ruthenium, iridium, and osmium.

4. A catalyst for use in an electrochemical reactor device, said catalyst comprising an alloy consisting essentially of a plurality of metals, said metals being selected from platinum, rhodium, ruthenium, iridium, and osmium, wherein said catalyst is an anode and said alloy comprises platinum in an atomic percent greater than about 11 and less than about 44, and one or more other metals selected from rhodium, ruthenium, and iridium.

5. A catalyst for use in an electrochemical reactor device, said catalyst comprising an alloy consisting essentially of a plurality of metals, said metals being selected from platinum, rhodium, ruthenium, iridium, and osmium, wherein said catalyst is a cathode and said alloy comprises ruthenium in an atomic percent greater than about 11 and less than about 88, and one or more other metals selected from rhodium, platinum, osmium, and iridium.

6. A cathode comprising an alloy, said alloy being selected from the group consisting of:
   (a) Pt(3.5)Ru(2)Os(2.5)Ir(1); and
   (b) Rh(4)Pt(2.5)Ru(1.5)Ir(1).

7. The catalyst of claim 2, wherein said catalyst further comprises an inorganic support.

8. The catalyst of claim 7, wherein said inorganic support is a carbon support.

9. An electrochemical reaction device comprising the catalyst of claim 2.

10. The device of claim 9, wherein said device is a fuel cell.

11. The catalyst of claim 2, wherein said catalyst further comprises an inorganic support.

12. The catalyst of claim 11, wherein said inorganic support is a carbon support.

13. An electrochemical reaction device comprising the catalyst of claim 2.

14. The device of claim 13, wherein said device is a fuel cell.

* * * * *